United States Patent [19]

Debono et al.

[11] 4,375,513

[45] Mar. 1, 1983

[54] BIOLOGICALLY PURE CULTURE OF ACTINOPLANES MISSOURIENSIS

[75] Inventors: Manuel Debono, Indianapolis; Kurt E. Merkel, Mooresville; Robert E. Weeks; Herald J. Cole, both of Indianapolis, all of Ind.

[73] Assignee: Eli Lilly and Company, Indianapolis, Ind.

[21] Appl. No.: 309,965

[22] Filed: Oct. 9, 1981

Related U.S. Application Data

[62] Division of Ser. No. 217,962, Dec. 18, 1980, Pat. No. 4,322,406.

[51] Int. Cl.$^3$ .......................... C12P 1/06; C12R 1/045
[52] U.S. Cl. ..................................... 435/169; 435/827
[58] Field of Search ......................... 435/169, 827, 170

[56] References Cited

U.S. PATENT DOCUMENTS

| | | | |
|---|---|---|---|
| 3,952,095 | 4/1976 | Hamill et al. | 424/118 |
| 4,064,233 | 12/1976 | Hamill et al. | 424/118 |
| 4,115,552 | 9/1978 | Hamill et al. | 424/118 |
| 4,239,751 | 12/1980 | Coronelli et al. | 435/169 |
| 4,303,646 | 12/1981 | Cavalleri et al. | 435/169 |

*Primary Examiner*—Alvin E. Tanenholtz
*Attorney, Agent, or Firm*—Gerald V. Dahling; Arthur R. Whale

[57] ABSTRACT

Antibiotic A-4696 factors $B_1$, $B_2$, $B_3$, $C_{1a}$, $C_3$, and $E_1$ are isolated from antibiotic A-4696, the latter being produced by *Actinoplanes missouriensis* strains ATCC 31680, ATCC 31682, and ATCC 31683 under submerged aerobic conditions in a culture medium and isolated from the fermentation broth by absorption on an ion exchange resin and eluted therefrom at $p^H$ 10.5 with sodium hydroxide. The novel factors are separated by thin layer chromatography and high pressure liquid chromatography and have antimicrobial and growth promotant activity.

2 Claims, 6 Drawing Figures

BIOLOGICALLY PURE CULTURE OF ACTINOPLANES MISSOURIENSIS

This application is a division of application Ser. No. 217,962, filed Dec. 18, 1980 now U.S. Pat. No. 4,322,406.

BACKGROUND OF THE INVENTION

The present invention is related generally to the inventions disclosed in U.S. Pat. No. 3,952,095 issued Apr. 20, 1976, for novel antibiotic and a process for the production thereof, U.S. Pat. No. 4,064,233 issued Dec. 20, 1977, for antibiotic A-4696, and U.S. Pat. No. 4,115,552 issued Sept. 19, 1978, for factor A and B of antibiotic A-4696.

Factor B of antibiotic A-4696, described in U.S. Pat. No. 4,064,233 and U.S. Pat. No. 4,115,552, is not the same as any of the factors claimed in the present application. Furthermore, none of the present antibiotic A-4696 factors were known, appreciated, or even suspected prior to the present invention. In fact the above patents teach that any additional factors or chromatographic spots are mere "artifacts of the chromatographic processes" and therefore teach away from the present invention.

SUMMARY OF THE INVENTION

The present invention relates to novel factors $B_1$, $B_2$, $B_3$, $C_{1a}$, $C_3$, and $E_1$, of actaplanin antibiotic A-4696. In accordance with the present invention novel factors of antibiotic A-4696 are isolated from antibiotic A-4696, the latter being produced by culturing a microorganism belonging to the genus Actinoplanes in a nutrient medium until substantial antibacterial activity is detected in the culture medium.

High performance liquid chromatography (HPLC) reveals that the antibiotic A-4696 complex as disclosed in related applications listed herein above, comprises several heretofore unknown factors designated as $B_1$, $B_2$, $B_3$, $C_{1a}$, and $C_3$. An additional factor, designated as $E_1$, can also be isolated from the antibiotic A-4696 complex and may represent a degradation product. The chemical, physical, and biological properties of the factors indicate that they are new antibiotics and, except possibly for factor $E_1$, that they are composed of the same peptide core (aglycone) and amino sugar, and varying amounts of glucose, mannose, and rhamnose. While factor $E_1$ is similar in most respects to the other factors, it is possible that it possesses a somewhat modified peptide core. Bioautography of aglycone formation during hydrolysis of both the A-4696 complex and the individual factors shows that within a short time a simple mixture of antimicrobially active pseudo-aglycone and aglycone is obtained. It is possible that the site of antimicrobial activity of the A-4696 complex and individual factors resides in the peptide pseudo-aglycone, with the factors being substantially differentiated by differences in their neutral sugar composition. The attached sugars may function chiefly to modulate solubility and other important pharmacodynamic parameters. However, the manner in which the antibiotic factors claimed herein function or are produced does not constitute a part of the invention, and applicant does not intend to be limited in any way by the postulated mode of action stated herein.

The antibiotic factors of this invention are isolated from antibiotic A-4696 which is produced by culturing the organism Actinoplanes missouriensis in an aqueous nutrient medium under submerged aerobic fermentation conditions. The antibiotic A-4696 complex is first separated from the fermentation broth and then the individual factors are isolated by liquid chromatography. Preferably the antibiotic factors of the present invention are converted to a hydrochloride or sulfate salt.

For purposes of the present application, the term 'antibiotic A-4696' is used to designate the actaplanin antibiotic complex, while the various factors isolated from the complex are designated as antibiotic A-4696 factors A, $B_1$, $B_2$, $B_3$, $C_{1a}$, $C_3$, $E_1$, and so forth. Antibiotic A-4696 and the individual factors isolated therefrom, are highly effective in preventing the growth of microorganisms which are pathogenic to both man and animals. In addition, the antibiotic factors of the present invention have agricultural application as growth promotants in chickens, swine, sheep, and beef cattle.

DETAILED DESCRIPTION OF THE INVENTION

Figure 1:
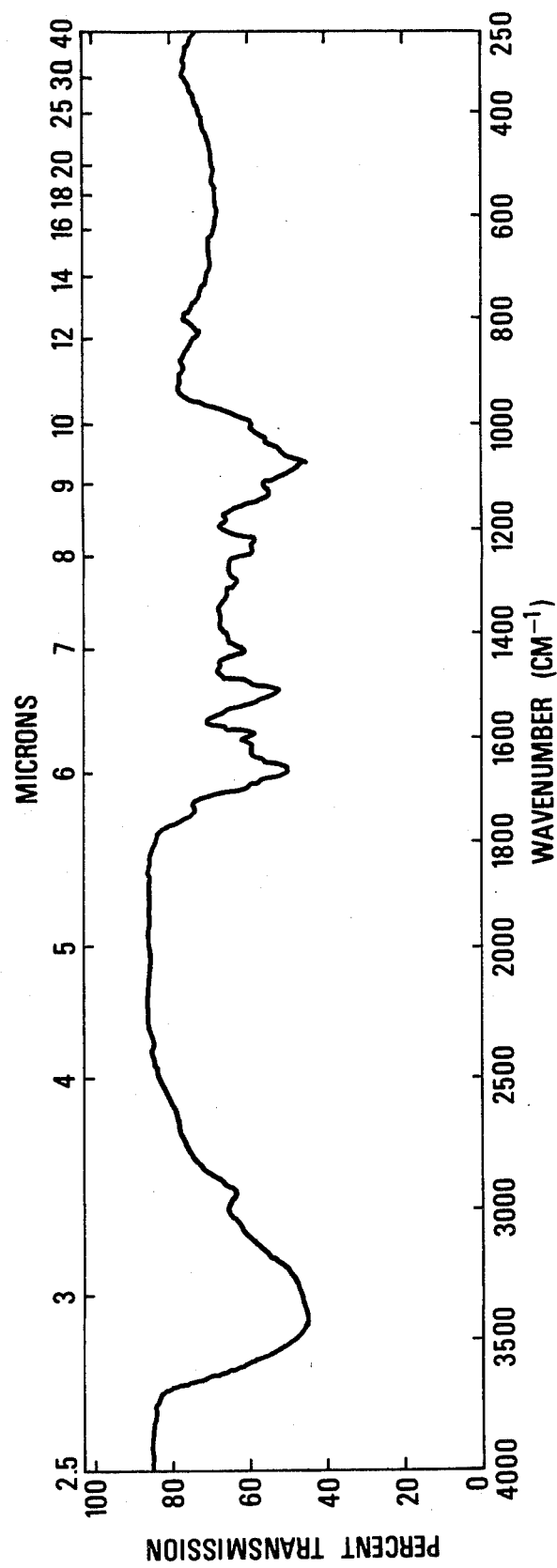

The present invention comprises novel antibiotic factors $B_1$, $B_2$, $B_3$, $C_{1a}$, $C_3$, and $E_1$ of antibiotic A-4696. The antibiotics are basic compounds capable of forming salts with suitable acids and are isolated from antibiotic A-4696 which is produced by culturing a microorganism belonging to the species Actinoplanes missouriensis in a nutrient medium until substantial antibacterial activity is detected in the culture medium. The characterization data presented below are for the antibiotic A-4696 factors in the form of their hydrochloride salts, although other pharmaceutically acceptable salts can also be prepared by employing methods known in the art.

Silica gel thin layer chromatography (TLC) bioautography and high pressure liquid chromatography (HPLC) reveal that antibiotic A-4696, when subjected to the isolation procedure, yields a mixture of several components which show antibiotic activity. The components, designated as antibiotic A-4696 factors A, $B_1$, $B_2$, $B_3$, $C_{1a}$, $C_3$, and $E_1$, can be preparatively separated from antibiotic A-4696 by chromatography through a polyamide column. The chromatography fractions are monitored by UV-activity and thin layer chromatography (TLC) and identical chromatography fractions containing the pure antibiotic A-4696 factor A, $B_1$, $B_2$, $B_3$, $C_{1a}$, $C_3$, or $E_1$ are combined and freeze dried. The identity and purity of the resulting freeze dried chromatography pools can be determined by HPLC.

Antibiotic A-4696 factor A was previously isolated and is substantially as disclosed in U.S. Pat. No. 4,115,552. Current data concerning this factor are presented only to help exemplify the separation and characterization of the other novel antibiotic A-4696 factors which constitute the subject matter of the present application.

Thin layer chromatography of antibiotic A-4696 with bio-overlay using methanol-chloroform-conc. ammonium hydroxide-sec. butanol-water (50:25:25:25:10) as the solvent, and Bacillus subtilis as the detection organism, gives the following results:

| A-4696 Factor | $R_f$-Value |
|---|---|
| A | 0.25 |
| $B_1$ | 0.35 |
| $B_2$ | 0.45 |
| $B_3$ | 0.40 |

| A-4696 Factor | $R_f$-Value |
|---|---|
| $C_{1a}$ | 0.51 |

High pressure liquid chromatography of antibiotic A-4696 at ambient temperature using 2% aqueous acetic acid/CH$_3$CN (90/10) and 2% aqueous acetic acid/CH$_3$CN (70/30) as the solvents gives the following results:

| A-4696 Factor | $K'$-Value |
|---|---|
| A | 1.60 |
| $B_1$ | 1.99 |
| $B_2$ | 3.84 |
| $B_3$ | 2.50 |
| $C_{1a}$ | 2.92 |
| $C_3$ | 4.23 |
| $E_1$ | .38 |

Several additional minor factors can also be separated from antibiotic A-4696 by employing TLC and HPLC. These factors are designated $C_{1b}$, $C_{2a}$, $C_{2b}$, and D and are similar in many respects to antibiotic A-4696 factors A, $B_1$, $B_2$, $B_3$, $C_{1a}$, $C_3$, and $E_1$. In addition there may be other as yet undetected factors in the antibiotic A-4696 complex. The minor factors have not been isolated and purified in sufficient quantity to allow for characterization.

When either antibiotic A-4696 or the individual antibiotic A-4696 factors are hydrolyzed under mild acidic conditions (5% methanolic HCl, reflux, 70 minutes) a pseudo-aglycone is produced. The pseudo-aglycone precipitates from the hydrolysis mixture and, in the case of antibiotic A-4696 factors A, $B_1$, $B_2$, $B_3$, $C_{1a}$, and $C_3$, has the following structure:

A-4696 factors A, $B_1$, $B_2$, $B_3$, and $C_{1a}$ are presented as follows:

TABLE 1

| | Molar Ratios of Neutral Sugars* | | |
|---|---|---|---|
| A-4696 Factor | Mannose | Glucose | Rhamnose |
| A | 2.80 | 1.0 | — |
| $B_1$ | 2.05 | 1.0 | 1.01 |
| $B_2$, | 1.80 | 1.0 | — |
| $B_3$, | 2.37 | 1.0 | — |
| $C_{1a}$, | 1.12 | 1.0 | 1.08 |

*Sugars determined by gas chromatographic analysis of their trimethylsilyl derivatives. Each sugar is the sum of its α and β-isomers.

The individual antibiotic A-4696 factors are substantially differentiated by their neutral sugar components which are attached to the pseudo-aglycone at unknown positions.

Antibiotic A-4696 factor $B_1$, as the hydrochloride salt, is a white crystalline compound which is soluble in water and hydroxylic and polar solvents, and insoluble in solvents such as ether, chloroform, benzene, acetone, aliphatic hydrocarbons, chlorinated hydrocarbons and the like. It is stable in aqueous solution over a pH range of about 4 to about 9 at temperatures up to about 27° C.

Microanalysis of antibiotic A-4696 factor $B_1$ hydrochloride of antibiotic A-4696 shows the following approximate elemental composition with oxygen comprising the remainder: C 51.51; H 5.25; N 4.88; Cl 4.62. The approximate molecular weight, theoretically determined by combining the molecular weights of the pseudo-aglycone and the known attached sugars, is 1954.

The ultraviolet absorption maximum of antibiotic A-4696 factor $B_1$ hydrochloride in water is at 280 nm with an $E_{1cm}^{1\%}$ of 42.8.

The infrared absorption spectrum of antibiotic A-4696 factor $B_1$ hydrochloride in KBr is shown in FIG.

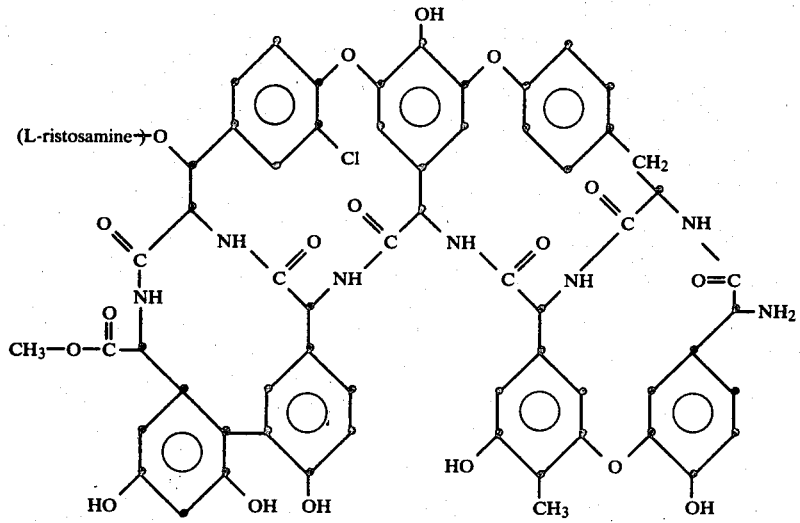

In the case of antibiotic A-4696 factor $E_1$, it is possible but not certain that the above pseudo-aglycone may be somewhat modified.

Paper and TLC examination of the hydrolysis filtrates of the antibiotic A-4696 complex and the individual antibiotic A-4696 factors reveals that, in addition to a pseudo-aglycone core, the complex and factors each contain varying amounts of neutral sugars. The identity and molar ratios of the neutral sugars found in antibiotic 1 of the accompanying drawings. The observed distinguishable absorption maximum over the range of 4000–700 cm$^{-1}$ are as follows: 3380 broad, 2930, 1731, 1693, 1654, 1637, 1615, 1588, 1577, 1521, 1503, 1488, 1423, 1321, 1289, 1229, 1210, 1178, 1154, 1121, 1076, 1060, 1030, 1012, 982, 880, 842, 831, 810 cm$^{-1}$.

Antibiotic A-4696 factor $B_2$, as the hydrochloride salt, is a white crystalline compound which is soluble in water and hydroxylic and polar solvents, and insoluble in solvents such as ether, chloroform, benzene, acetone, aliphatic hydrocarbons, chlorinated hydrocarbons and the like. It is stable in aqueous solution over a pH range of about 4 to about 9 at temperatures up to about 27° C.

Microanalysis of antibiotic A-4696 factor $B_2$ hydrochloride shows the following approximate elemental composition with oxygen comprising the remainder: C 51.96; H 4.67; N 5.72; Cl 5.88. The approximate molecular weight, theoretically determined by combining the molecular weights of the pseudo-aglycone and the known attached sugars, is 1808.

The ultraviolet absorption maximum of antibiotic A-4696 factor $B_2$ hydrochloride in water is at 280 nm with an $E_{1cm}^{1\%}$ of 44.7.

Figure 2:
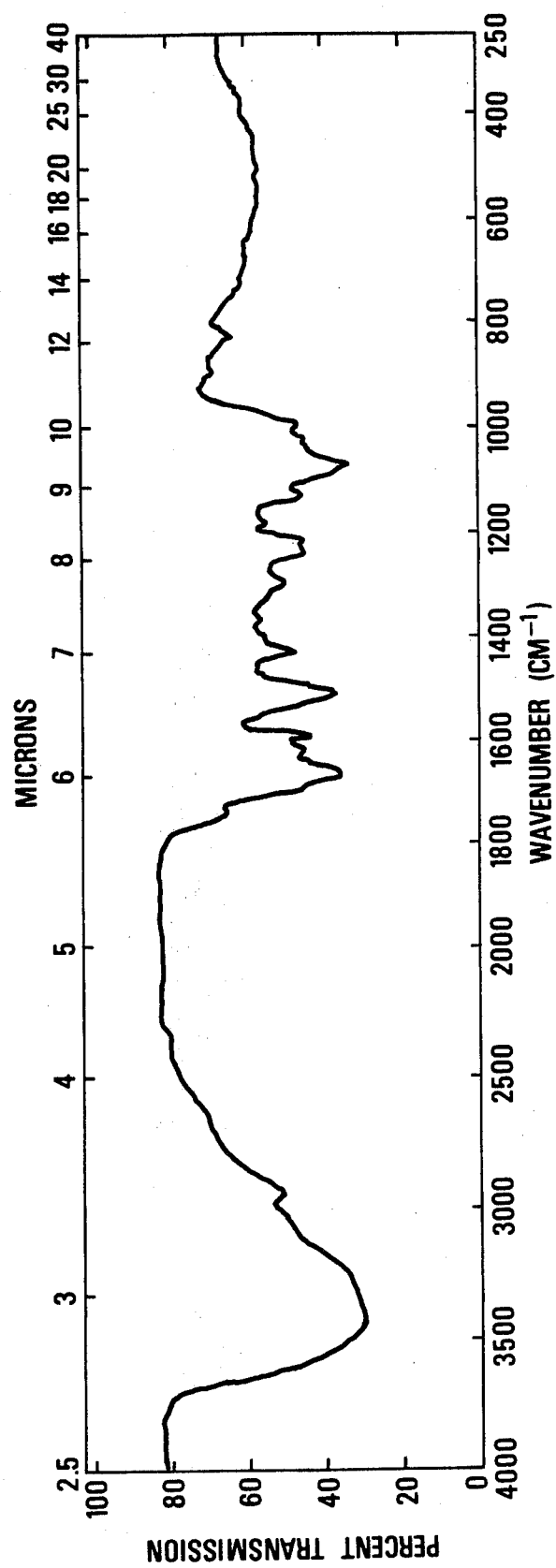

The infrared absorption spectrum of antibiotic A-4696 factor $B_2$ hydrochloride in KBr is shown in FIG. 2 of the accompanying drawings. The observed distinguishable absorption maxima over the range of 4000–700 cm$^{-1}$ are as follows: 3409 broad, 2934, 1730, 1658, 1614, 1588, 1548, 1504, 1498, 1490, 1426, 1290, 1231, 1210, 1179, 1121, 1061, 1031, 1017, 987, 903, 884, 818 cm$^{-1}$.

Antibiotic A-4696 factor $B_3$, as the hydrochloride salt, is a white crystalline compound which is soluble in water and hydroxylic and polar solvents, and insoluble in solvents such as ether, chloroform, benzene, acetone, aliphatic hydrocarbons, chlorinated hydrocarbons and the like. It is stable in aqueous solution over a pH range of about 4 to about 9 at temperatures up to about 27° C.

Microanalysis of antibiotic A-4696 factor $B_3$ hydrochloride shows the following approximate elemental composition with oxygen comprising the remainder: C 51.84; H 4.74; N 5.83; Cl 5.57. The approximate molecular weight, theoretically determined by combining the molecular weights of the pseudo-aglycone and the known attached sugars, is 1808.

The ultraviolet absorption maximum of antibiotic A-4696 factor $B_3$ hydrochloride in water is at 280 nm with an $E_{1\,cm}^{1\%}$ of 46.3.

Figure 3:
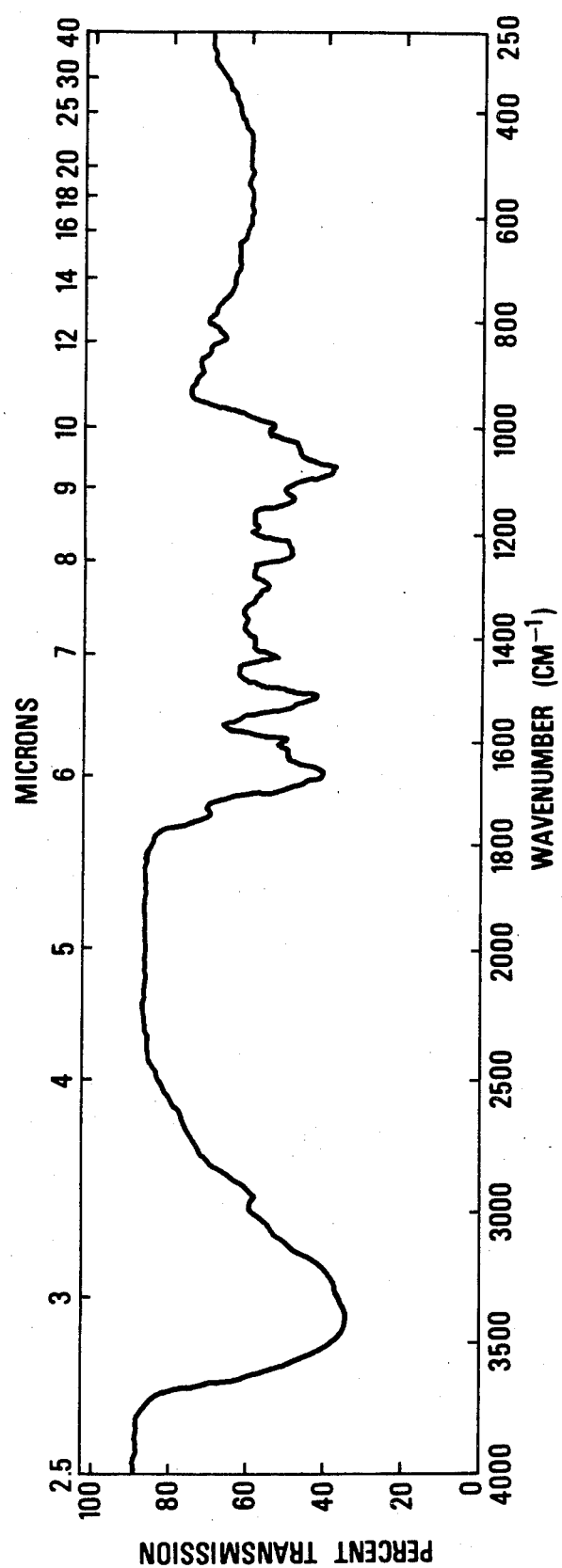

The infrared absorption spectrum of antibiotic A-4696 factor $B_3$ hydrochloride in KBr is shown in FIG. 3 of the accompanying drawings. The observed distinguishable absorption maxima over the range of 4000–700 cm$^{-1}$ are as follows: 3394 broad, 2938, 1733, 1697, 1675, 1656, 1638, 1614, 1591, 1515, 1504, 1489, 1427, 1359, 1291, 1228, 1209, 1180, 1120, 1072, 1051, 1018, 985, 903, 882, 846, 816 cm$^{-1}$.

Antibiotic A-4696 factor $C_{1a}$, as the hydrochloride salt, is a white crystalline compound which is soluble in water and hydroxylic and polar solvents, and insoluble in solvents such as ether, chloroform, benzene, acetone, aliphatic hydrocarbons, chlorinated hydrocarbons and the like. It is stable in aqueous solution over a pH range of about 4 to about 9 at temperatures up to about 27° C.

Microanalysis of antibiotic A-4696 factor $C_{1a}$ hydrochloride shows the following approximate elemental composition with oxygen comprising the remainder: C 53.05; H 4.74; N 5.83; Cl 5.39. The approximate molecular weight theoretically determined by combining the molecular weight of the pseudo-aglycone and the known attached sugars, is 1792.

The ultraviolet absorption maximum of antibiotic A-4696 factor $C_{1a}$ hydrochloride in water is at 279 nm with an $E_{1\,cm}^{1\%}$ of 47.9.

Figure 4:
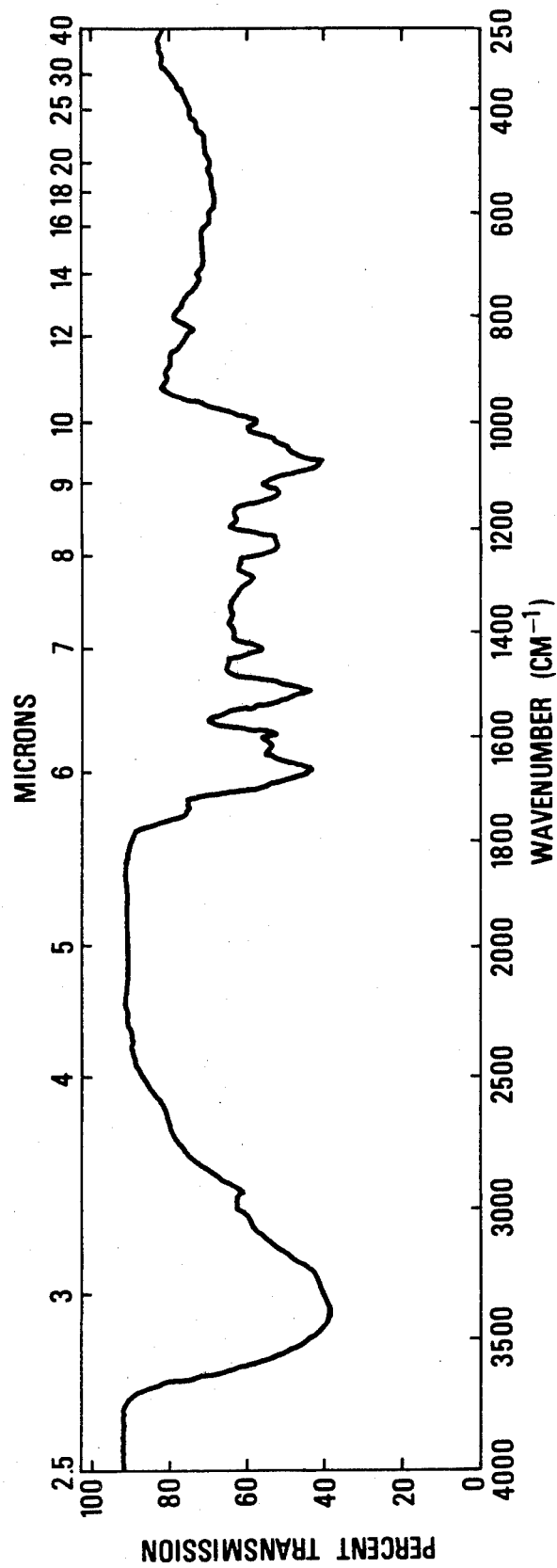

The infrared absorption spectrum of antibiotic A-4696 factor $C_{1a}$ hydrochloride in KBr is shown in FIG. 4 of the accompanying drawings. The observed distinguishable absorption maxima over the range of 4000–700 cm$^{-1}$ are as follows: 3380 broad, 2931, 1734, 1650, 1616, 1591, 1505, 1491, 1427, 1359, 1290, 1228, 1213, 1177, 1123, 1072, 1061, 1032, 1017, 987, 903, 832, 814, 715 cm$^{-1}$.

Antibiotic A-4696 factor $C_3$, as the hydrochloride salt, is a white crystalline compound which is soluble in water and hydroxylic and polar solvents, and insoluble in solvents such as ether, chloroform, benzene, acetone, aliphatic hydrocarbons, chlorinated hydrocarbons and the like. It is stable in aqueous solution over a pH range of about 4 to about 9 at temperatures up to about 27° C.

Microanalysis of antibiotic A-4696 factor $C_3$ hydrochloride shows the following approximate elemental composition with oxygen comprising the remainder: C, 51.73; H, 4.69; N, 5.94; Cl, 6.02.

The ultraviolet absorption maximum of antibiotic A-4696 factor $C_3$ hydrochloride in water is at 280 nm with an $E_{1\,cm}^{1\%}$ of 47.9.

Figure 5:
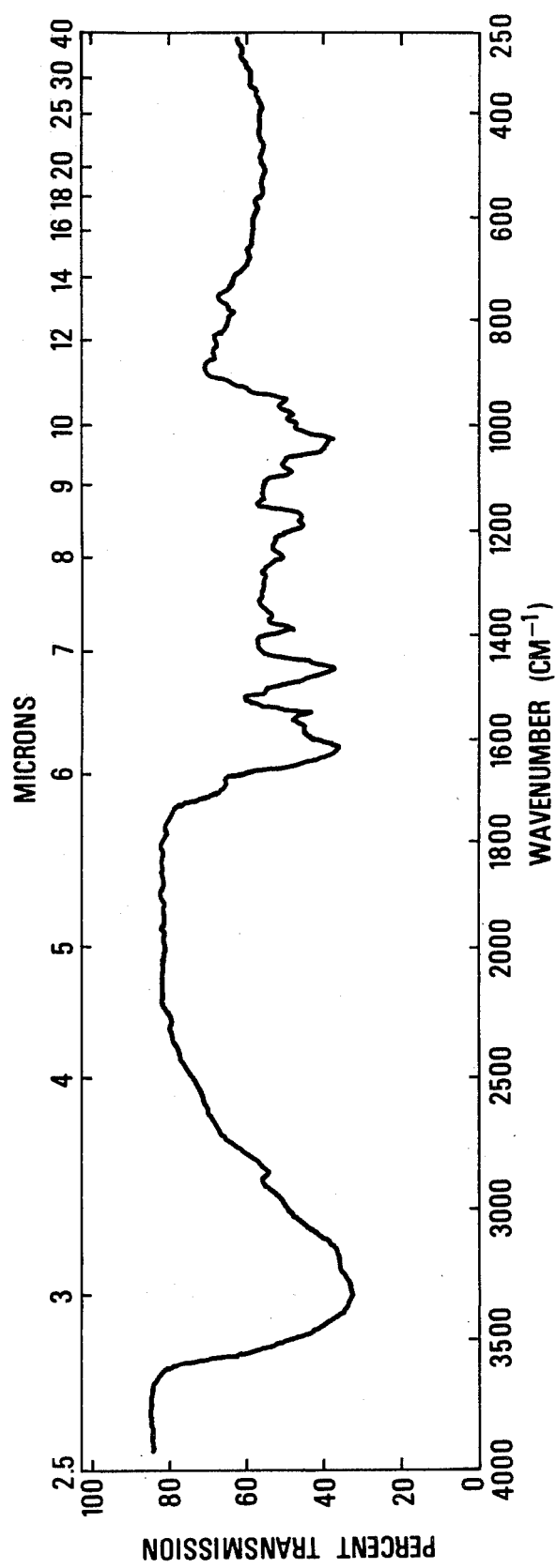

The infrared absorption spectrum of antibiotic A-4696 factor $C_3$ hydrochloride in KBr is shown in FIG. 5 of the accompanying drawings. The observed distinguishable absorption maxima over the range of 4000–700 cm$^{-1}$ are as follows: 3378 broad, 2925, 1728, 1689, 1658, 1637, 1616, 1589, 1579, 1573, 1546, 1536, 1529, 1523, 1503, 1489, 1474, 1457, 1426, 1421, 1397, 1387, 1286, 1231, 1206, 1121, 1075, 1062, 1028, 1012, 987, 965, 949, 878, 840, 816, 769, 708 cm$^{-1}$.

Antibiotic A-4696 factor $E_1$, as the hydrochloride salt, is a white crystalline compound which is soluble in water and hydroxylic and polar solvents, and insoluble in solvents such as ether, chloroform, benzene, acetone, aliphatic hydrocarbons, chlorinated hydrocarbons and the like. It is stable in aqueous solution over a pH range of about 4 to about 9 at temperatures up to about 27° C.

Microanalysis of antibiotic A-4696 factor $E_1$ hydrochloride shows the following approximate elemental composition with oxygen comprising the remainder: C 50.71; H 4.70; N 9.01; Cl 1.84.

The ultraviolet absorption maximum of antibiotic A-4696 factor $E_1$ hydrochloride in water is at 279 nm with an $E_{1\,cm}^{1\%}$ of 39.9.

Figure 6:
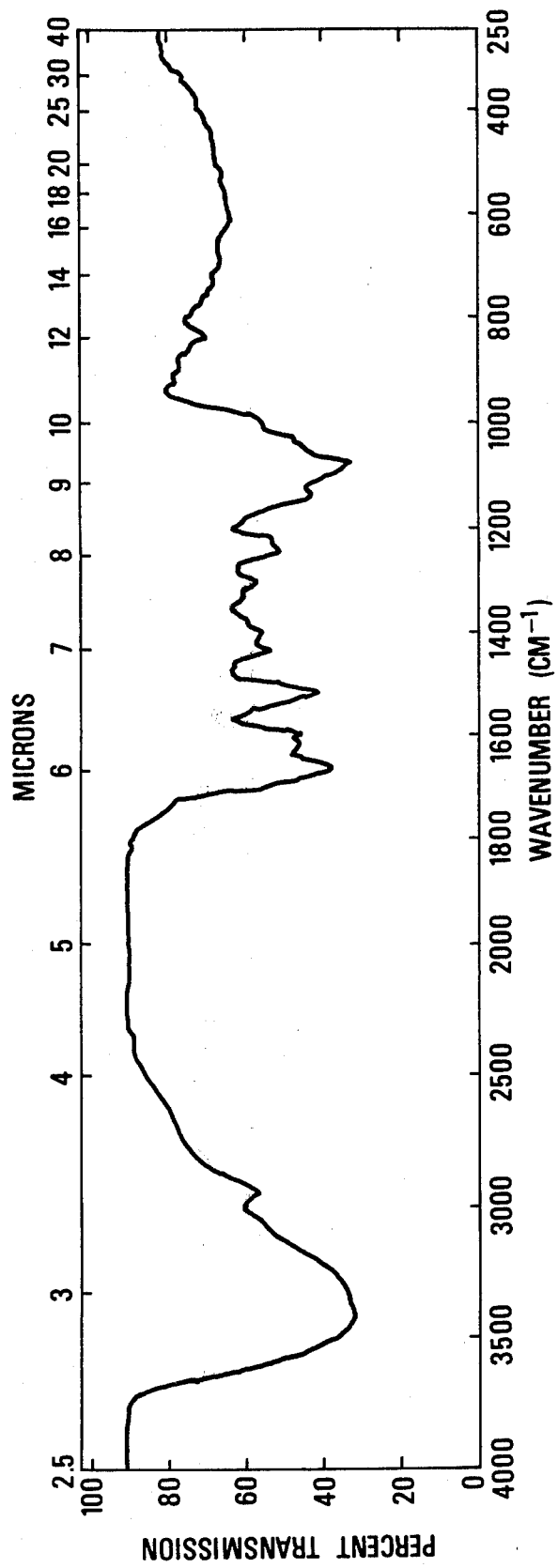

The infrared absorption spectrum of antibiotic A-4696 factor $E_1$ hydrochloride in KBr is shown in FIG. 6 of the accompanying drawings. The observed distinguishable absorption maxima over the range of 4000–700 cm$^{-1}$ are as follows: 3394 broad, 2933, 1657, 1636, 1610, 1589, 1538, 1511, 1505, 1453, 1424, 1393, 1369, 1328, 1320, 1291, 1232, 1212, 1178, 1120, 1075, 1061, 1031, 1018, 986, 973, 904, 878, 847, 813, 770, 752, 738, 714 cm$^{-1}$.

The antibiotic activity of antibiotic A-4696 factor $B_1$, $B_2$, $B_3$, $C_{1a}$, $C_3$, or $E_1$ hydrochloride has been established as being substantially the same as that exhibited by antibiotic A-4696 (disclosed in U.S. Pat. No. 4,115,552) against *Bacillus subtilis*.

By employing methods known in the art, pharmaceutically acceptable salts of antibiotic A-4696 factors $B_1$, $B_2$, $B_3$, $C_{1a}$, $C_3$, and $E_1$ can be prepared with mineral acids such as hydrochloric, hydrobromic, sulfonic, phosphoric, and the like. The antibiotic salts of such acids can be prepared, for example, by acidifying a solution of the antibiotic free-base with the desired acid and then precipitating the salt by introducing acetone to the solution. The salts can likewise be prepared in certain instances by ion exchange on an ion exchange column. Other known methods for the preparation of antibiotic salts can also be employed.

The novel antibiotic A-4696 factors have an inhibiting action on the growth of many microbial organisms which are pathogenic to man, animals and plants, and are therefore useful in suppressing the growth of such organisms. The levels at which antibiotic A-4696 factors $B_1$, $B_2$, $B_3$, $C_{1a}$, $C_3$, and $E_1$ as hydrochlorides show inhibition against the growth of illustrative organisms are set forth numerically in Tables 1 and 2 below. The inhibition levels were determined by the agar-dilution test and are stated in terms of the minimum inhibitory concentration (MIC), microgram(s) per milliliter (mcg./ml.).

In the agar-dilution test the test organism is streaked or implanted on agar plates containing various concentrations of antibiotic A-4696 factor hydrochlorides in the agar. The test plates are incubated at 37° C. for 48 hours, and the MIC is determined as the plate at the lowest concentration of the antibiotic where growth of the test organism is inhibited.

The results are as follows:

TABLE 1

| Test Organism (Bacteria) | Minimal Inhibitory Concentration - Agar Dilution Method Actaplanin Factor (μg./ml.) | | | |
|---|---|---|---|---|
| | $B_1$ | $B_2$ | $B_3$ | $C_{1a}$ |
| Staphylococcus epi Hitchens[1] | 32 | 8 | 2 | 2 |
| Staphylococcus epi Dutt. | 0.25 | 0.25 | 0.06 | 0.13 |
| Staphylococcus epi Bennet | 16 | 4 | 2 | 1 |
| Staphylococcus aureus 4283 | 16 | 4 | 1 | 1 |
| Staphylococcus aureus 3055 | 4 | 2 | 1 | 1 |
| Staphylococcus aureus 3132 | 16 | 4 | 2 | 2 |
| Staphylococcus aureus H25 | 4 | 2 | 2 | 1 |
| Staphylococcus aureus 3134 | 8 | 4 | 2 | 2 |
| Staphylococcus aureus 3123 | 8 | 4 | 1 | 2 |
| Staphylococcus aureus H535 | 8 | 4 | 2 | 2 |
| Staphylococcus aureus 3131 | 8 | 4 | 2 | 1 |
| Streptococcus Group D 282 | 2 | 2 | 0.5 | 0.5 |
| Streptococcus Group D 238 | 2 | 2 | 0.5 | 0.5 |
| Streptococcus Group D SS992 | 2 | 1 | 0.5 | 0.5 |
| Streptococcus Group D 9901 | 2 | 2 | 0.5 | 0.5 |
| Streptococcus Group D 9913 | 2 | 2 | 0.5 | 0.5 |
| Streptococcus Group D 9933 | 2 | 2 | 0.5 | 0.5 |
| Streptococcus Group D Guze | 2 | 1 | 0.5 | 0.5 |
| Streptococcus Group D 12753F | 2 | 2 | 0.5 | 0.5 |
| Streptococcus viridans 9943[2] | 0.5 | 1 | 0.25 | 0.5 |
| Streptococcus viridans 9961 | 1 | 1 | 0.5 | 0.5 |
| Streptococcus pyogenes C203 | 0.5 | 0.5 | 0.25 | 0.5 |
| Streptococcus pyogenes DS663-72 | 0.5 | 0.5 | 0.5 | 0.5 |
| Streptococcus pyogenes DS664-72 | 0.5 | 0.5 | 0.5 | 0.5 |
| Streptococcus pneumoniae Park I | 0.5 | 0.5 | 0.5 | 0.5 |
| Streptococcus pneumoniae Type 14 | 0.5 | 0.5 | 0.5 | 0.5 |
| Staphylococcus aureus 3074 | 32 | 8 | 4 | 8 |
| Streptococcus faecalis X66 | 1 | 1 | <0.5 | 2 |
| Proteus morganii PR15 | >128 | >128 | >128 | >128 |
| Salmonella typhosa SA12 | >128 | >128 | >128 | >128 |
| Klebsiella pneumoniae KL14 | >128 | >128 | >128 | >128 |
| Enterobacter aerogenes EB17 | >128 | >128 | >128 | >128 |
| Serratia marcescens SE3 | >128 | >128 | >128 | >128 |
| Eschericia coli EC14 | >128 | >128 | >128 | >128 |
| Citrobacter freundii CF17 | >128 | >128 | >128 | >128 |
| Pseudomonas aeruginosa X239 | >128 | >128 | >128 | >128 |
| Bordetella bronchiseptica 16 | >128 | >128 | >128 | >128 |
| Salmonella typhimurium | >128 | >128 | >128 | >128 |
| Pseudomonas solanacearum X185 | >128 | >128 | >128 | >128 |
| Erwinia amylovora | 64 | 128 | 128 | 128 |
| Candida tropicalis A17 | >128 | >128 | >128 | >128 |
| Trichophyton mentacrophytes 27 | >128 | >128 | >128 | >128 |
| Aspergillus flavus E | >128 | >128 | >128 | >128 |
| Ceratocystis ulmi | >128 | >128 | >128 | >128 |

[1]MH Agar Inoculum 1:500
[2]MH Agar Inoculum 1:10 5% Rabbit Blood

TABLE 2

| Test Organism (Bacteria) | Minimal Inhibitory Concentration-Agar Solution Method Actaplanin Factor (mg./ml.) | |
|---|---|---|
| | $C_3$ | $E_1$ |
| Staphylococcus aureus X1.1 | 2 | 16 |
| Staphylococcus aureus V41 | 1 | 16 |
| Staphylococcus aureus X400 | 2 | 16 |
| Staphylococcus aureus S13E | 2 | 16 |
| Staphylococcus epidermidis 1 | 2 | 32 |
| Staphylococcus epidermidis 2 | 1 | 16 |
| Streptococcus Group A C203 | .5 | 1 |
| Streptococcus Group D X66 | 1 | 4 |
| Streptococcus Group D 9960 | 2 | 8 |
| Streptococcus pneumoniae park | .5 | 2 |
| Haemophilus influenzae sens. C.L. | 32 | >128 |
| Haemophilus influenzae res. 76 | 64 | >128 |
| Shigella sonnei N9 | >128 | >128 |
| E. coli N10 | >128 | >128 |
| E. coli EC14 | >128 | >128 |
| E. coli TEM | 128 | >128 |
| Klebsiella X26 | >128 | >128 |
| Klebsiella KAE | >128 | >128 |
| Enterobacter aerogenes X68 | >128 | >128 |
| Enterobacter aerogenes C32 | >128 | >128 |
| Enterobacter aerogenes EB17 | >128 | >128 |
| Enterobacter cloacae EB5 | >128 | >128 |
| Enterobacter cloacae 265A | >128 | >128 |
| Salmonella typhosa X514 | >128 | >128 |
| Salmonella typhosa 1335 | >128 | >128 |
| Pseudomonas aeruginosa X528 | >128 | >128 |
| Pseudomonas aeruginosa X239 | >128 | >128 |
| Pseudomonas aeruginosa Ps18 | >128 | >128 |
| Serratia marcescens X99 | >128 | >128 |
| Serratia marcescens SE3 | >128 | >128 |
| Proteus morganii PR15 | >128 | >128 |
| Proteus inconstans PR33 | >128 | >128 |
| Proteus rettgeri PR7 | >128 | >128 |
| Proteus rettgeri C24 | >128 | >128 |
| Citrobacter freundii CF17 | >128 | >128 |
| Bordetella fronchiseptica 16 | >128 | >128 |
| Clostridium difficile 2994 | 1 | 1 |
| Clostridium perfringens 81 | 1 | 1 |
| Clostridium septicum 1128 | 1 | 1 |
| Eubacteruim aerofaciens 1235 | 1 | 1 |
| Peptococcus asaccharolyticus 1302 | .5 | 1 |
| Peptococcus prevoti 1281 | 128 | 128 |
| Peptostreptococcus anaerobius 1428 | >128 | >128 |
| Peptostreptococcus intermedius 1264 | 2 | 4 |
| Propionibacterium acnes 79 | 1 | 1 |
| Bacteroides frogilis 111 | 128 | >128 |
| Bacteroides fragilis 1877 | 128 | >128 |
| Bacteroides fragilis 1936B | 64 | 128 |
| Bacteroides thetaiotaomicron 1438 | 64 | >128 |
| Bacteroides melaninogenicus 1856/28 | >128 | >128 |
| Bacteroides melaninogenicus 2736 | 128 | >128 |
| Bacteroides vulgatis 1211 | 128 | >128 |
| Bacteroides corrodens 1874 | 128 | >128 |
| Fusobacterium symbiosum 1470 | 32 | 128 |
| Fusobacterium necrophorum 6054A | 128 | >128 |

Antibiotic A-4696 factors $B_1$, $B_2$, $B_3$, $C_{1a}$, $C_3$, and $E_1$ hydrochlorides, as seen from the above data, are effective antibacterial and antimicrobial agents which are useful for combating pathogenic microorganisms generally. In addition, the incorporation of antibiotic A-4696 factor $B_1$, $B_2$, $B_3$, $C_{1a}$, $C_3$, or $E_1$ or the acid addition salts thereof, into an appropriate toothpaste, gel, powder, or the like, or a suitable mouthwash, or other oral hygiene preparation, can provide an effective method for inhibiting the development of dental caries and periodontal disease which are associated with bacterial action. Alternatively, a solution of one or more antibiotic A-4696 factors or an acid addition salt thereof at an appropriate concentration, can be applied to the surface of the gums and teeth with a suitable swab.

Antibiotic A-4696 factors $B_1$, $B_2$, $B_3$, $C_{1a}$, $C_3$, and $E_1$ also show growth promotant activity and accelerate the growth rate and increase feed efficiency in poultry, swine, sheep, and beef cattle. For example, the daily ingestion by poultry and swine of one or more antibiotics of the present invention in an amount of about 0.5 mg. to about 25 mg./kg. of body weight, results in faster growth and greater feed efficiency than that registered by animals fed the same basal ration without the active agent. The term "basal ration" refers to the total feed intake of the animal and consists of the various feedstuffs, concentrates, supplements, minerals, vitamins or medicated premixes, roughages, and the like containing the dietary requirements of the animal. Typical basal rations for poultry and swine are found in U.S. Pat. No. 4,115,552.

In an important embodiment of the present invention, antibiotic A-4696 factor $B_1$, $B_2$, $B_3$, $C_{1a}$, $C_3$, or $E_1$, or a suitable derivative or mixture thereof, is administered orally in a suitable feed in an amount of about 2 to 200 grams per ton of total feed to provide for increased feed efficiency and growth promotion activity. The addition of the active antibiotic A-4696 factors of this invention to animal feed is preferably accomplished by preparing an appropriate feed premix (such as, for example, is disclosed in U.S. Pat. No. 4,115,552) containing about 1 to 100 grams of antibiotic A-4696 factor $B_1$, $B_2$, $B_3$, $C_{1a}$, $C_3$, or $E_1$, or a suitable derivative or mixture thereof, per pound of premix. The completed premix is then incorporated into the final ration. Alternatively, an intermediate concentrate or feed supplement containing the active agent can be blended into the feed.

While the novel antibiotic A-4696 factors $B_1$, $B_2$, $B_3$, $C_{1a}$, $C_3$, and $E_1$ are useful in several different ways, they are particularly effective as antibiotics. Substances which exhibit this type of activity are always in demand for the treatment of microbially related health problems generally.

The novel antibiotic factors of this invention are isolated from antibiotic A-4696, the latter being produced by culturing one of several strains of Actinoplanes under aerobic conditions in a suitable culture medium until the culture medium contains substantial antibiotic activity. The antibiotic factors can be recovered by employing various appropriate isolation and purification procedures.

The microorganism used for the production of antibiotic A-4696 has been identified as a strain of *Actinoplanes missouriensis* of the family Actinoplanaceae. The Actinoplanaceae are a family of microorganisms of the order Actinomycetales, having been first described by Dr. John N. Couch, Jour. Elisha Mitchell Sci. Soc., 65, 315–318 (1949); and 66, 87–92 (1950); Trans. New York Acad. Sci., 16, 315–318 (1954); Jour. Elisha Mitchell Sci. Soc., 71, 148–155 and 269 (1955); Bergey's Manual of Determinative Bacteriology, 7th Edition, 825–829 (1957); and Jour. Elisha Mitchell Sci. Soc., 79, 53–70 (1963).

Biologically pure cultures of the *Actinoplanes missouriensis* strains useful for the production of antibiotic A-4696 for subsequent isolation of antibiotic A-4696 factors $B_1$, $B_2$, $B_3$, $C_{1a}$, $C_3$, and $E_1$ have been deposited and made part of the stock culture collection of the American Type Culture Collection, Rockville, Maryland, from which they are available to the public without restriction under the numbers ATCC 31680, ATCC 31682, and ATCC 31683. Strain ATCC 31682 is useful for production of antibiotic A-4696 for subsequent isolation of antibiotic A-4696 factors $B_1$ and $C_{1a}$; strain ATCC 31680 for isolation of antibiotic A-4696 factors $B_2$ and $C_3$; and strain ATCC 31683 for isolation of antibiotic A-4696 factors $B_3$ and $E_1$.

*Actinoplanes missouriensis* strains ATCC 31680, ATCC 31682, and ATCC 31683 are characterized by the physical and cultural properties set forth in the following paragraphs.

The three strains are derived by a series of mutations from ATCC 23342 which was previously disclosed in U.S. Pat. No. 4,115,552. The present strains produce in similar substrate or mycelium and their morphology is substantially indistinguishable from that of the parental strain. Neither aerial, secondary mycelia, nor sporangia are observed and moreover, techniques such as growth on pollen grains, likewise fails to yield any sporangia.

The main differences between the present strains are the cultural characteristics, specifically the pigmentation of the primary mycelia. Strain ATCC 31680 has an orange colored mycelium ranging from moderate to brownish orange to strong orange depending upon the medium. Strains ATCC 31682 and ATCC 31683 have no such distinctive color and show mycelia which are yellowish gray.

The methods used for the taxonomic studies of strains ATCC 31680, ATCC 31682, and ATCC 31683 are well known to those skilled in the art and in large part are methods recommended for the International Streptomyces Project (ISP), described by Shirling and Gottlieb, 1966, Intern. J. of Systematic Bacteriol. 16(3):313–340. Enzyme assays were carried out according to the methods of Blazevic and Ederer, 1975, Principles of Biochemical Tests in Diagnostic Microbiology, John Wiley and Sons. Inc., New York, and color names, abbreviations, and numbers were assigned using the ISCC-NBS method of Kelly and Judd, 1976, The ISCC-NBS Centroid Color Charts Standard Sample No. 2106, U.S. Dept. of Commerce, National Bureau of Standards, Washington D.C. Lysozyme resistance and the decomposition of casein, esculin, hypoxanthine, tyrosine, and xanthine were measured using the procedure of Berg, 1973, Appl. Microbiol. 25:665–681. Carbon utilization studies were also completed and are stored as follows:

++ = equal to or > glycose control; positive utilization

+ = < glucose control, > no carbon control; positive utilization (+) = growth questionable; doubtful utilization − = no growth; negative utilization Accordingly a taxonomic description, including both the cultural and physiological characteristics, of the Actinoplanes strains of the present invention is given in tabular form below.

| General Culture And Physiological Characteristics Of Actinoplanes Strain ATCC 31680 | |
|---|---|
| Property Observed | Characteristics |
| Culture characteristics on: | |
| ISP medium no. 2 | Growth abundant, reverse 76. l.yBr; no aerial mycelium; no soluble pigment. |
| ISP medium no. 3 | Growth good, reverse 93. yGray; no aerial mycelium; no soluble pigment. |
| ISP medium no. 4 | Growth good, reverse 53.m.O; no aerial mycelium; no soluble pigment. |
| ISP medium no. 5 | Growth good, shiny, reverse 50.s.O; no aerial mycelium; no |

| General Culture And Physiological Characteristics Of Actinoplanes Strain ATCC 31680 | |
|---|---|
| Property Observed | Characteristics |
| | soluble pigment. |
| ISP medium no. 7 | Growth good, reverse 54.brO; no aerial mycelium; soluble pigment light brown. |
| Bennett's agar | Growth abundant, reverse 53.m.O; no aerial mycelium; no soluble pigment. |
| Calcium malate | Growth good, shiny, reverse 50.s.O; no aerial mycelium; no soluble pigment. |
| Czapek's agar | Growth good, reverse 50.s.O; no aerial mycelium; no soluble pigment. |
| Glucose - Asparagine | Growth fair, reverse 53.m.O; no aerial mycelium; no soluble pigment. |
| Tomato paste - oatmeal | Growth abundant, reverse 53.m.O; no aerial mycelium; no soluble pigment. |
| Anio - Hensens's agar | Growth poor, reverse 93.yGray; no aerial mycelium; no soluble pigment. |
| 53H medium | Growth poor, reverse 91.d.gyY; no aerial mycelium; no soluble pigment. |
| Czapek's peptone | Growth abundant, reverse 54.brO; no aerial mycelium; no soluble pigment. |
| Casein decomposition | Positive |
| Catalase reaction | Positive |
| Esculin decomposition | Positive |
| Gelatin liquefaction | Negative |
| $H_2S$ production in ISP medium no. 6 | Trace |
| Hypoxanthine decomposition | Negative |
| Lysozyme resistance | Negative |
| Melanoid pigments on | |
| ISP medium no. 1 | Negative |
| ISP medium no. 6 | Negative |
| ISP medium no. 7 | Negative |
| ISP medium no. 7 minus tyrosine | Negative |
| NaCl tolerance on ISP medium no. 2 | 2% |
| Nitrate reduction | Negative |
| $p^H$ growth range on ISP medium no. 2 | 6-8.4 |
| Phosphatase production | Positive |
| Skim milk reaction | Negative |
| Starch hydrolysis on ISP medium no. 4 | Negative |
| Sucrose tolerance on ISP medium no. 2 | 20% |
| Temperature growth range on ISP medium no. 2 | 5-37° C. |
| Tyrosine decomposition | Negative |
| Urease production | Positive |
| Antibiotic sensitivity: | |
| Cephalothin (sodium) 30 μg. | Sensitive |
| Erythromycin (estolate) 15 μg. | Sensitive |
| Chloromycetin 30 μg. | Sensitive |
| Novobiocin 30 μg. | Sensitive |
| Penicillin (G) 10 units | Sensitive |
| Rifampin 5 μg. | Sensitive |
| Streptomycin 10 μg. | Sensitive |
| Tetracycline 30 μg. | Sensitive |
| Vancomycin HCl 30 μg. | Sensitive |
| Xanthine production | Negative |
| Carbon utilization on ISP medium no. 9* with: | |
| no carbon | − |
| glucose | ++ |
| L-arabinose | ++ |
| cellobiose | ++ |
| D-fructose | ++ |
| D-galactose | ++ |
| i-inositol | − |

| General Culture And Physiological Characteristics Of Actinoplanes Strain ATCC 31680 | |
|---|---|
| Property Observed | Characteristics |
| D-mannitol | + |
| melibiose | + |
| raffinose | + |
| D-rhamnose | ++ |
| D-ribose | (+) |
| salicin | + |
| sucrose | + |
| D-xylose | ++ |
| Antibiotic A-4696 factor production | $B_2$ and $C_3$ |

*Sterilized carbon sources were added to equal a final concentration of 1.0%.

| General Culture And Physiological Characteristics Of Actinoplanes Strain ATCC 31682 | |
|---|---|
| Property Observed | Characteristics |
| Culture characteristics on: | |
| ISP medium no. 2 | Growth good, reverse 90.gy.Y; no aerial mycelium; no soluble pigment. |
| ISP medium no. 3 | Growth good, reverse 93.yGray; no aerial mycelium; no soluble pigment. |
| ISP medium no. 4 | Growth good, reverse 79.1.gy.yBr; no aerial mycelium; no soluble pigment. |
| ISP medium no. 5 | Growth good, shiny, reverse 90.gy.Y; no aerial mycelium; no soluble pigment. |
| ISP medium no. 7 | Growth fair, reverse 80.gy.yBr; no aerial mycelium; no soluble pigment. |
| Bennett's agar | Growth abundant, reverse 93.yGray; no aerial mycelium; no soluble pigment. |
| Calcium malate | Growth good, shiny, reverse 93.yGray; no aerial mycelium; no soluble pigment. |
| Czapek's agar | Growth abundant, reverse 93.yGray; no aerial mycelium; no soluble pigment. |
| Glucose - Asparagine | Growth good, reverse 93.yGray; no aerial mycelium; no soluble pigment. |
| Tomato paste - oatmeal | Growth abundant, reverse 91.d.gy.Y; no aerial mycelium; no soluble pigment. |
| Anio - Hensen's agar | Growth fair, reverse 91.d.gy.Y; no aerial mycelium; no soluble pigment. |
| 53H medium | Growth good, reverse 91.d.gy.Y; no aerial mycelium, no soluble pigment. |
| Czapek's peptone | Growth abundant, reverse 90.gy.Y; no aerial mycelium; no soluble pigment. |
| Casein decomposition | Positive |
| Catalase reaction | Positive |
| Esculin decomposition | Positive |
| Gelatin liquefaction | Positive (100%) |
| $H_2S$ production in ISP medium no. 6 | Trace |
| Hypoxanthine decomposition | Negative |
| Lysozyme resistance | Negative |
| Melanoid pigments on | |
| ISP medium no. 1 | Negative |
| ISP medium no. 6 | Negative |
| ISP medium no. 7 | Negative |
| ISP medium no. 7 minus tyrosine | Negative |
| NaCl tolerance on ISP medium no. 2 | 2% |
| Nitrate reduction | Negative |
| $p^H$ growth range on | |

General Culture And Physiological Characteristics Of Actinoplanes Strain ATCC 31682

| Property Observed | Characteristics |
|---|---|
| ISP medium no. 2 | 6–8 |
| Phosphatase production | Positive |
| Skim milk reaction | Negative |
| Starch hydrolysis on ISP medium no. 4 | Negative |
| Sucrose tolerance on ISP medium no. 2 | 20% |
| Temperature growth range on ISP medium no. 2 | 10–37° C. |
| Tyrosine decomposition | Positive |
| Urease production | Positive |
| Antibiotic sensitivity: | |
| Cephalothin (sodium) 30 μg. | Sensitive |
| Erythromycin (estolate) 15 μg. | Sensitive |
| Chloromycetin 30 μg. | Sensitive |
| Novobiocin 30 μg. | Sensitive |
| Penicillin (G) 10 units | Sensitive |
| Rifampin 5 μg. | Sensitive |
| Streptomycin 10 μg. | Sensitive |
| Tetracycline 30 μg. | Sensitive |
| Vancomycin HCl 30 μg. | Sensitive |
| Xanthine production | Negative |
| Carbon utilization on ISP medium no. 9* with: | |
| no carbon | − |
| glucose | ++ |
| L-arabinose | ++ |
| cellobiose | ++ |
| D-fructose | ++ |
| D-galactose | ++ |
| i-inositol | − |
| D-mannitol | ++ |
| melibiose | + |
| raffinose | + |
| D-rhamnose | + |
| D-ribose | + |
| salicin | + |
| sucrose | + |
| D-xylose | ++ |
| Antibiotic A-4696 factor production | A, $B_1$, $B_2$, and $C_{1a}$ |

*Sterilized carbon sources were added to equal a final concentration of 1.0%.

General Culture And Physiological Characteristics Of Actinoplanes Strain ATCC 31683

| Property Observed | Characteristics |
|---|---|
| Culture characteristics on: | |
| ISP medium no. 2 | Growth good, reverse 90.gy.Y; no aerial mycelium; no soluble pigment. |
| ISP medium no. 3 | Growth good, reverse 93. yGray; no aerial mycelium; no soluble pigment. |
| ISP medium no. 4 | Growth good, reverse 79.1.gy.yBr; no aerial mycelium; no soluble pigment. |
| ISP medium no. 5 | Growth fair, reverse 90.gy.Y; no aerial mycelium; no soluble pigment. |
| ISP medium no. 7 | Growth fair, reverse 80.gy.yBr; no aerial mycelium; soluble pigment light brown. |
| Bennett's agar | Growth abundant, reverse 93.yGray; no aerial mycelium; no soluble pigment. |
| Calcium malate | Growth good, shiny, reverse 93.yGray; no aerial mycelium; no soluble pigment. |
| Czapek's agar | Growth abundant, reverse 93.yGray; no aerial mycelium; no soluble pigment. |
| Glucose - asparagine | Growth good, reverse 93.yGray; no aerial mycelium; no soluble pigment. |
| Tomato paste - oatmeal | Growth good, reverse 91.d.gy.Y; no aerial mycelium; no soluble pigment. |
| Anio - Hensen's agar | Growth fair, reverse 91.d.gy.Y; no aerial mycelium; no soluble pigment. |
| 53H medium | Growth good, reverse 91.d.gy.Y; no aerial mycelium; no soluble pigment. |
| Czapek's peptone | Growth abundant, reverse 90.gy.Y; no aerial mycelium; no soluble pigment. |
| Casein decomposition | Positive |
| Catalase reaction | Positive |
| Esculin decomposition | Positive |
| Gelatin liquefaction | Positive (100%) |
| $H_2S$ production in ISP medium no. 6 | Trace |
| Hypoxanthine decomposition | Negative |
| Lysozyme resistance | Negative |
| Melanoid pigments on | |
| ISP medium no. 1 | Negative |
| ISP medium no. 6 | Negative |
| ISP medium no. 7 | Negative |
| ISP medium no. 7 minus tyrosine | Negative |
| NaCl tolerance on ISP medium no. 2 | <2% |
| Nitrate reduction | Negative |
| $p^H$ growth range on ISP medium no. 2 | 6–8.4 |
| Phosphatase production | Positive |
| Skim milk reaction | Negative |
| Starch hydrolysis on ISP medium no. 4 | Negative |
| Sucrose tolerance on ISP medium no. 2 | 20% |
| Temperature growth range on ISP medium no. 2 | 5–40° C. |
| Tyrosine decomposition | Positive |
| Urease production | Negative |
| Antibiotic sensitivity: | |
| Cephalothin (sodium) 30 μg. | Sensitive |
| Erythromycin (estolate) 15 μg. | Sensitive |
| Chloromycetin 30 μg. | Sensitive |
| Novobiocin 30 μg. | Sensitive |
| Penicillin (G) 10 units | Sensitive |
| Rifampin 5 μg. | Sensitive |
| Streptomycin 10 μg. | Sensitive |
| Tetracycline 30 μg. | Sensitive |
| Vancomycin HCl 30 μg. | Sensitive |
| Xanthine production | Negative |
| Carbon utilization on ISP medium no. 9* with: | |
| no carbon | − |
| glucose | ++ |
| L-arabinose | ++ |
| cellobiose | ++ |
| D-fructose | ++ |
| D-galactose | ++ |
| i-inositol | − |
| D-mannitol | ++ |
| melibiose | + |
| raffinose | + |
| D-rhamnose | + |
| D-ribose | + |
| salicin | + |
| sucrose | + |
| D-xylose | ++ |
| Antibiotic A-4696 factor production | A, $B_1$, $B_2$, and $B_3$ |

*Sterilized carbon sources were added to equal a final concentration of 1.0%.

As previously noted, *Actinoplanes missouriensis* strains ATCC 31680, ATCC 31682, and ATCC 31683 can be grown in a culture medium to produce antibiotic A-4696 for subsequent isolation of the antibiotic A-4696 factors. The culture medium can be any one of a number of different media. However for economy in production, maximum yield, and ease of isolation of the antibiotic, certain culture media are preferred. Thus, for example, starch is one of the preferred sources of carbohydrate, and yeast is one of the preferred nitrogen sources. Other carbohydrates sources which can be used include molasses, glucose, dextrin, glycerol, and the like. Nitrogen sources also include amino acid mixtures, peptones, and the like.

Nutrient inorganic salts to be incorporated in the culture medium can include the customary salts capable of yielding sodium, potassium, ammonia, calcium, phosphate, chloride, sulfate, and like ions. Additionally, sources of growth factors, such as distillers' solubles and yeast extracts, can be included with beneficial effect on the production of antibiotic A-4696 factors.

As is necessary for the growth and development of other microorganisms, essential trace elements should also be included in the culture medium for growing the Actinoplanes strains employed in this invention. Such trace elements are commonly supplied as impurities incidental to the addition of the other constituents of the medium.

The organisms used to produce antibiotic A-4696 for subsequent isolation of antibiotic A-4696 factors $B_1$, $B_2$, $B_3$, $C_{1a}$, $C_3$, and $E_1$ can be grown over a relatively wide pH range. However it is desirable to culture the organisms in a medium with a pH between about 6.5 and 7.0. As with other Actinomycetes, the pH of the growing medium gradually changes during the growth period, the pH at the end of the fermentation period usually ranging from about 6.5 to 7.5.

Submerged aerobic cultural conditions are preferred for the production of the antibiotic A-4696 factors. Relatively small amounts of the antibiotics can be produced by shake flask culture; however, for the preparation of large amounts, submerged aerobic culture in sterile tanks is preferred. The culture medium in the sterile tank can be inoculated with a mycelial fragment suspension.

Accordingly, it is desirable to produce a vegetative inoculum of the organism by inoculating a relatively small quantity of culture medium with the mycelial fragments of the organism, and when a young active vegetative inoculum is obtained, to aseptically transfer it to the large tank. The medium in which the vegetative inoculum is grown can be the same as that utilized for large scale production of the antibiotic A-4696 factors, although other media can be employed.

The antibiotic A-4696 factor producing *Actinoplanes missouriensis* strains ATCC 31680, ATCC 31682, and ATCC 31683, grow at temperatures between 20° and 40° C. The largest amounts of A-4696 factors appear to be produced at a temperature of about 30° C.

Sterile air is blown through the culture medium in the submerged aerobic culture process. The volume of air sparged into the culture medium varies from about 0.1 to about 1.0 volume of air per minute per volume of culture medium. The most efficient growth and antibiotic production are achieved when the volume of air is at least ½ volume of air per minute per volume of culture medium.

The rate of production of antibiotic A-4696 factors and the concentration of antibiotic activity in the culture medium can be followed during the growth period by testing samples of the fermentation broth for antibiotic activity against organisms known to be susceptible to the antibiotic. One such assay organism useful to illustrate the present invention is *Bacillus subtilis*. The bioassay can be carried out by the standard cup-plate methods, or by the paper disc assay on agar plates.

Generally, maximum production of the antibiotic occurs within about 4 to 6 days in shake flasks or submerged aerobic culture fermentations.

Antibiotic A-4696 for subsequent isolation of antibiotic A-4696 factors $B_1$, $B_2$, $B_3$, $C_{1a}$, $C_3$, and $E_1$ can be isolated from the culture medium and separated from other substances which may be present by adsorptive and extractive techniques. Adsorptive techniques are preferred because such procedures avoid the use of large volume of solvents required in extraction processes.

Since the procedures for exemplifying the present invention are substantially the same when using strains ATCC 31680 (for isolation of antibiotic A-4696 factors $B_2$ and $C_3$), ATCC 31682 (for isolation of antibiotic A-4696 factors $B_1$ and $C_{1a}$), and ATCC 31683 (for isolation of antibiotic A-4696 factors $B_3$ and $E_1$), the use of only ATCC 31682 is presented here for simplicity. Certain procedural differences relating to the production medium and the use of strain ATCC 31683 are also presented in Example 1 where appropriate. Accordingly this invention is exemplified by the following examples:

EXAMPLE 1

A. Shake Flask Fermentation

Mycelial fragments of *Actinoplanes missouriensis*, illustrated here with strain ATCC 31682 for simplicity, were inoculated on a nutrient agar slant having the following composition:

| Ingredient | Amount |
| --- | --- |
| Cerelose | 0.5% |
| Potato dextrin | 2.0% |
| *Nutrisoy flour | 1.5% |
| Yeast extract | 0.25% |
| CaCO₃ | 0.1% |
| Agar | 2.0% |

*Nutrisoy flour is obtained from Archer Daniels Midland Company, 4666 Faries Parkway, Decatur, Illinois 62526.

The slant inoculated with ATCC 31682 was then incubated for 6 days at 30° C. The culture does not sporulate so it is necessary to macerate the mycelial mat with a sterile pipette. The macerated mature culture was covered with sterile distilled water and scraped carefully with the pipette or a sterile rod to obtain a mycelial suspension.

The suspension thus obtained was used to inoculate 100 ml. of a sterile vegetative medium having the following composition:

| Ingredient | Amount |
| --- | --- |
| Cerelose | 0.5% |
| Potato dextrin | 2.0% |
| Nutrisoy flour | 1.5% |
| Yeast extract | 0.25% |

-continued

| Ingredient | Amount |
|---|---|
| CaCO$_3$ | 0.1% |

The inoculated vegetative medium was grown for 48 hours at 30° C. on a rotary shaker operating at 250 rpm. Ten ml. of the inoculated vegetative medium was inoculated into 100 ml. of a sterile "bump" medium of the following composition.

| Ingredient | Amount |
|---|---|
| Cerelose | 0.5% |
| Yeast | 0.25% |
| Nutrisoy flour | 1.5% |
| Corn starch | 2.0% |
| CaCO$_3$ | 0.1% |
| Sag 471 | 0.05% |

The inoculated "bump" medium was incubated for 24 hours at 30° C. with constant shaking on a rotary shaker operating at 250 rpm.

Four-tenths ml. of the "bump" medium was inoculated into 100 ml. portions of a production medium of the composition shown below contained in 500 ml. Erlenmeyer flasks, and sterilized at 121° C. for 30 minutes.

| Ingredient | Amount |
|---|---|
| Cerelose | 1.0% |
| Corn starch | 3.5% |
| Sucrose | 3.0% |
| Molasses | 1.5% |
| Yeast | 1.0% |
| Proflo (Cotton seed flour) | 1.0% |
| CaCO$_3$ | 0.2% |
| K$_2$HPO$_4$ | 0.05% |
| (NH$_4$)$_2$SO$_4$ | 0.025% |
| MgSO$_4$.7H$_2$O | 0.5% |
| Sag 471 | 0.03% |

The production fermentation was shaken for about 96 hours at a temperature of 30° C. on a rotary shaker operating at 250 rpm. The pH at the end of the fermentation cycle was about 8.0.

For production of antibiotic A-4696 factors B$_3$ and E$_1$, strain ATCC 31683 was used to prepare the "bump" medium according to the teaching disclosed above. Four-tenths ml. of the strain ATCC 31683 "bump" medium was inoculated into 100 ml. portions of a production medium of the composition shown below contained in 500 ml. Erlenmeyer flasks, and sterilized at 121° C. for 30 minutes.

| Ingredient | Amount |
|---|---|
| Cerelose | 1.0% |
| Yeast | 2.0% |
| CaCO$_3$ | 0.2% |
| K$_2$HPO$_3$ | 0.05% |
| (NH$_4$)$_2$SO$_4$ | 0.025% |
| Sag 471 | 0.03% |

The production fermentation was shaken for about 96 hours at a temperature of 30° C. on a rotary shaker operating at 250 rpm. The pH at the end of the fermentation cycle was about 8.0.

B. 40-Liter Tank Fermentation

The preparation of the inoculum proceeded through the incubation of the "bump" medium detailed under section A, above. Twenty-five liters of a production medium as outlined above, was sterilized by autoclaving at 121° C. for 30 minutes and charged into a 40 l. capacity fermentation tank. One-hundred ml. of "bump" medium was inoculated into the sterile production medium. The inoculated production medium was allowed to ferment for 4 days at 30° C. The fermentation was aerated with sterile air in an amount of about one-half volume of air per volume of culture medium per minute. The fermenting production medium was agitated with a mixer utilizing an impeller to insure adequate mixing of air with the medium. The pH of the culture medium gradually increased from an initial level of about 6.5 to about 8.0 as the fermentation proceeded.

C. Isolation of Antibiotic A-4696

Fermentation broth (3800 l.) prepared according to the above procedure was filtered after the addition of 5% (wt/vol) filter aid (Celite 545). The filter cake was resuspended in deionized water (3600 l.) and the pH of the aqueous suspension was adjusted to pH 10.5 using aqueous sodium hydroxide. The suspended solids were separated by filtration and washed with water. The filtrate and the washings were combined and the resulting solution was acidified with 20% (wt/vol) aqueous sulfuric acid to pH 4.5. The acidic solution was clarified by filtration using 1% filter aid (Celite 545). The clear solution was passed through a column (1.8×5 ft.) containing 350 l. of Amberlite IR-116 (Na+ form) and the column was washed with deionized water (1200 l.). The IR-116 resin was removed from the column and eluted batchwise at pH 10.5 with an aqueous solution of sodium hydroxide (total 1000 liters). The resin eluate was neutralized (pH 7) with 20% (wt/vol) aqueous sulfuric acid, then washed with three portions of deionized water (150 liters total). The water washes were neutralized and combined with the neutralized eluate. The resulting solution was concentrated and subsequently freeze dried. The preparation of the crude complex varied in color from tan to dark brown.

D. Removal of Salts from Crude Antibiotic A-4696

The crude complex (1.0 kg) was slowly added with vigorous stirring to deionized water (1.5 liters). The resulting suspension was stirred for twenty minutes and was subsequently neutralized (pH 7) using a 10% aqueous ammonium hydroxide solution. The insoluble antibiotic A-4696 complex was separated by vacuum filtration, washed with deionized water, and freeze dried. The dried, desalted, complex was recovered in approximately 80% yield (based on bioactivity).

E. Purification of Desalted Antibiotic A-4696

The dried, desalted complex (300 g.) was suspended in deionized water (2 liters), and the pH of the suspension was adjusted to pH 2.7 by addition of 3 N aqueous hydrochloric acid. The acidified solution was centrifuged for 40 minutes at 2500 rpm. The supernatant was decanted and loaded on a column (8×85 cm) containing 6 liters of decolorizing resin (Duolite S761). The activity was eluted with deionized water at a flow rate of 30 ml/min. The elution was monitored by thin layer chromatography. The antibiotic A-4696-containing effluent was concentrated (3 mm., 35° C.) to a volume of 3 liters and freeze dried. The decolorized complex was recovered as a white-to-tan solid in approximately 70% yield (based on bioactivity).

F. Isolation of Antibiotic A-4696 Factors $B_1$, $B_2$, $B_3$, $C_{1a}$, $C_3$, and $E_1$ Hydrochloride Salts The dried, decolorized antibiotic A-4696 complex (10 g.) was dissolved in 100 ml. of deionized water. The resulting aqueous solution was filtered and loaded on a chromatography column (5×100 cm.) containing 2 liters of polyamide (Machery & Nagel SC6). The column was eluted with deionized water and 200–300 fractions (25 ml. each) were collected. The elution was monitored by UV-activity and by thin layer chromatography. Fractions were combined according to TLC identity and freeze dried. For some of the separations it was necessary to double the column length (200 cm.) by using two of the polyamide columns in line. Additional purification was achieved by repeated chromatography.

The procedures outlined in A–F above are followed using strain ATCC 31682, when isolation of antibiotic A-4696 factors $B_1$ and $C_{1a}$ is desired, using strain ATCC 31680 when isolation of A-4696 factors $B_2$ and $C_3$ is desired, and using strain ATCC 31683 when isolation of antibiotic A-4696 factors $B_3$ and $E_1$ is desired. While other Actinoplanes strains may be used for isolation of the above aforementioned factors, the strains disclosed are preferred for isolation of the antibiotic A-4696 factors claimed herein.

An alternative method for isolating antibiotic A-4696 factors $B_1$, $B_2$, $B_3$, $C_{1a}$, $C_3$, and $E_1$ as hydrochloride salts using a single *Actinoplanes missouriensis* strain is as follows:

The dried, decolorized antibiotic A-4696 complex (200 mg. prepared from Strain 31683 according to the teaching of Example 1, A–E above) was dissolved in about 2 ml. distilled water. The resulting aqueous solution was filtered and separated by column chromatography using reversed phase adsorbents such as, for example, Li Chroprep® RP-18* as the stationary phase and aqueous acetonitrile gradients containing triethylamine phosphate as the mobile phase. Although it is understood that those skilled in the art will vary the acetonitrile concentration gradient depending upon the composition of a particular fermentation, a preferred concentration gradient is 10–40%. The column effluent was monitored by UV-activity and fractions containing the individual factors were collected. The acetonitrile was removed by evaporation under high vacuum and the resulting aqueous solutions were freeze dried. The freeze dried chromatography fractions were then redissolved in distilled water, adsorbed on reversed phase adsorbents such as, for example, Sep Rak® C18 cartridges** and eluted with 50% aqueous methanol. The aqueous solutions containing the individual antibiotic A-4696 factors were evaporated to dryness and the purified antibiotic A-4696 factors were then recovered as dry amorphous solids.

*Available from E. Merck, Darmstadt, Germany
**Available from Waters Associates Inc., Milford, Massachusetts

EXAMPLE 2

Preparation of Antibiotic A-4696 factors $B_1$, $B_2$, $B_3$, $C_{1a}$, $C_3$, and $E_1$ as Sulfate Salts Antibiotic A-4696 (300 g. prepared according to the teaching of Example 1, A–D) was suspended in deionized water (2 liters), and the pH of the suspension was adjusted to pH 2.7 by addition of 3 N aqueous sulfuric acid. The acidified solution was centrifuged for 40 minutes at 2500 rpm. The supernatant was decanted and loaded on a column (8×85 cm) containing 6 liters of decolorizing resin (Duolite S761). The activity was eluted with deionized water at a flow rate of 30 ml./min. The elution was monitored by thin layer chromatography. The antibiotic A-4696-containing effluent was concentrated (3 mm., 35° C.) to a volume of 3 liters and freeze dried. The decolorized complex was recovered as a white-to-tan solid in approximately 70% yield (based on bioactivity). The individual A-4696 factors $B_1$, $B_2$, $B_3$, $C_{1a}$, $C_3$, and $E_1$ sulfates were isolated according to the teaching of Example 1, F.

I claim:

1. The biologically pure culture of *Actinoplanes missouriensis* strain ATCC 31683 which when cultured in a nutrient medium under submerged aerobic fermentation conditions, produces antibiotic A-4696 for the subsequent isolation of antibiotic A-4696 factors $B_1$ and $C_{1a}$.

2. The biologically pure culture of *Actinoplanes missouriensis* strain ATCC 31683 which when cultured in a nutrient medium under submerged aerobic fermentation conditions, produces antibiotic A-4696 for the subsequent isolation of antibiotic A-4696 factors $B_3$ and $E_1$.

* * * * *

UNITED STATES PATENT AND TRADEMARK OFFICE
CERTIFICATE OF CORRECTION

PATENT NO. : 4,375,513
DATED : March 1, 1983
INVENTOR(S) : Manuel Debono et al.

It is certified that error appears in the above-identified patent and that said Letters Patent are hereby corrected as shown below:

Column 20, line 38, in Claim 1, "ATCC 31683" should read
--ATCC 31682--.

Signed and Sealed this

Twenty-second Day of May 1984

[SEAL]

Attest:

GERALD J. MOSSINGHOFF

Attesting Officer

Commissioner of Patents and Trademarks